(12) United States Patent
He et al.

(10) Patent No.: US 6,839,506 B2
(45) Date of Patent: Jan. 4, 2005

(54) METHODS AND APPARATUS FOR A DISCRETE VAPOR-DISPENSING DEVICE

(75) Inventors: Mengtao Pete He, Scottsdale, AZ (US); Carl Triplett, Scottsdale, AZ (US); Mary Conway, Phoenix, AZ (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

(21) Appl. No.: 10/640,103

(22) Filed: Aug. 13, 2003

(65) Prior Publication Data

US 2004/0105667 A1 Jun. 3, 2004

Related U.S. Application Data

(63) Continuation-in-part of application No. 10/222,079, filed on Aug. 16, 2002.

(51) Int. Cl.⁷ .................................................. F24F 6/08
(52) U.S. Cl. ...................................... 392/392; 392/395
(58) Field of Search ................................ 392/386, 390, 392/392, 393, 395; 261/142, DIG. 65; 239/34, 44, 45, 135, 136

(56) References Cited

U.S. PATENT DOCUMENTS

| | | |
|---|---|---|
| 1,836,600 A | 12/1931 | Jones |
| 3,262,290 A | 7/1966 | Huber |
| 3,748,438 A | 7/1973 | Costello |
| 3,780,260 A | 12/1973 | Eisner |

(List continued on next page.)

FOREIGN PATENT DOCUMENTS

| | | |
|---|---|---|
| DE | 35 35 564 | 5/1986 |
| DE | 41 31 613 | 3/1993 |
| EP | 0 296 807 | 12/1988 |
| EP | 0 669 137 | 8/1995 |
| EP | 0 911 041 | 4/1999 |
| GB | 402507 | 12/1933 |
| GB | 2 356 815 | 6/2001 |
| WO | WO 00 76292 | 12/2000 |
| WO | WO 01 10739 | 2/2001 |
| WO | WO 01/68154 | 9/2001 |
| WO | WO 01/93919 | 12/2001 |

OTHER PUBLICATIONS

PCT International Search Report issued Dec. 17, 2003 for International Application No. PCT/US03/26511, International Filing Date Aug. 26, 2003, 4 pages.
PCT International Search Report issued Apr. 21, 2004 for International Application No. PCT/US03/26754, International Filing Date Aug. 28, 2003, 4 pages.
PCT International Search Report issued Nov. 12, 2003 for International Application No. PCT/US03/25245, International Filing Date Aug. 13, 2003, 4 pages.

*Primary Examiner*—Sang Paik
(74) *Attorney, Agent, or Firm*—Snell & Wilmer L.L.P.

(57) ABSTRACT

A vapor-dispensing or other environment-altering apparatus is configured to integrate with a receptacle in a discreet manner. In accordance with one embodiment of the invention, an environment-altering apparatus is configured to mimic an electrical receptacle having an outlet pattern. The environment-altering apparatus has a front surface which includes an outlet pattern substantially corresponding to the outlet pattern of the electrical receptacle, and a plug configured to interface with the electrical receptacle. A device configured to modify one or more attributes of the environment is interposed between the front surface and plug pattern. These attributes include, for example, aromatic vapor density, insecticide vapor density, ambient light intensity, ionic air content, ultrasonic frequency intensity, and the like.

7 Claims, 10 Drawing Sheets

U.S. PATENT DOCUMENTS

| | | |
|---|---|---|
| 3,895,928 A | 7/1975 | Gonzalo |
| 3,908,905 A | 9/1975 | Von Philipp et al. |
| 3,923,458 A | 12/1975 | Gonzalo |
| 3,948,445 A | 4/1976 | Andweg |
| 4,017,030 A | 4/1977 | Coplan et al. |
| 4,037,353 A | 7/1977 | Hennart et al. |
| 4,084,079 A | 4/1978 | Costello |
| 4,111,655 A | 9/1978 | Quincey |
| 4,123,741 A | 10/1978 | Kiyono et al. |
| 4,165,835 A | 8/1979 | Dearling |
| 4,171,340 A | 10/1979 | Nishimura et al. |
| 4,208,012 A | 6/1980 | Dutcher |
| 4,214,146 A | 7/1980 | Schimanski |
| 4,220,281 A | 9/1980 | Martens, III et al. |
| 4,228,124 A | 10/1980 | Kashihara et al. |
| 4,243,969 A | 1/1981 | Steigerwald et al. |
| 4,293,173 A | 10/1981 | Tricca |
| 4,294,778 A | 10/1981 | DeLuca |
| 4,346,059 A | 8/1982 | Spector |
| 4,391,781 A | 7/1983 | Van Lit |
| 4,408,813 A | 10/1983 | Koehler |
| 4,413,779 A | 11/1983 | Santini |
| 4,415,797 A | 11/1983 | Choustoulakis |
| 4,425,302 A | 1/1984 | Pons Pons |
| 4,467,177 A | 8/1984 | Zobele et al. |
| 4,518,212 A | 5/1985 | Rumble |
| 4,530,556 A | 7/1985 | Bonus |
| 4,537,351 A | 8/1985 | Wilson |
| 4,544,592 A | 10/1985 | Spector |
| 4,549,250 A | 10/1985 | Spector |
| 4,556,539 A | 12/1985 | Spector |
| 4,571,485 A | 2/1986 | Spector |
| 4,574,181 A | 3/1986 | Spector |
| 4,595,564 A | 6/1986 | Spector et al. |
| 4,631,387 A | 12/1986 | Glucksman |
| 4,658,985 A | 4/1987 | Madsen et al. |
| 4,660,764 A | 4/1987 | Joyaux et al. |
| 4,662,679 A | 5/1987 | Franck |
| 4,675,504 A | 6/1987 | Suhajda |
| 4,686,353 A | 8/1987 | Spector |
| 4,695,434 A | 9/1987 | Spector |
| 4,703,155 A | 10/1987 | Suhajda |
| 4,707,336 A | 11/1987 | Jones |
| 4,714,984 A | 12/1987 | Spector |
| 4,718,856 A | 1/1988 | Pinkerton et al. |
| 4,725,712 A | 2/1988 | Schroeder |
| 4,731,520 A | 3/1988 | Glucksman |
| 4,731,522 A | 3/1988 | Manchester |
| 4,732,321 A | 3/1988 | Dolan |
| 4,734,560 A | 3/1988 | Bowen |
| 4,739,928 A | 4/1988 | O'Neil |
| 4,743,406 A | 5/1988 | Steiner et al. |
| 4,753,389 A | 6/1988 | Davis |
| 4,777,345 A | 10/1988 | Manchester |
| 4,780,286 A | 10/1988 | Parent et al. |
| 4,795,883 A | 1/1989 | Glucksman et al. |
| 4,798,935 A | 1/1989 | Pezaris |
| 4,800,239 A | 1/1989 | Hill |
| 4,801,271 A | 1/1989 | Piper |
| 4,804,821 A * | 2/1989 | Glucksman .................. 392/390 |
| 4,808,347 A | 2/1989 | Dawn |
| 4,816,973 A | 3/1989 | Atalla et al. |
| 4,830,791 A | 5/1989 | Muderlak et al. |
| 4,837,421 A | 6/1989 | Luthy |
| 4,849,606 A | 7/1989 | Martens, III et al. |
| 4,853,517 A | 8/1989 | Bowen et al. |
| 4,878,615 A | 11/1989 | Losi |
| 4,886,469 A | 12/1989 | Jseng |
| 4,915,301 A | 4/1990 | Munteanu |
| 4,919,981 A | 4/1990 | Levey et al. |
| 4,931,224 A | 6/1990 | Holzner, Sr. |
| 4,931,258 A | 6/1990 | Zlotnik et al. |
| 4,968,456 A | 11/1990 | Muderlak et al. |
| D315,789 S | 3/1991 | Muderlak |
| 4,998,671 A | 3/1991 | Leifheit |
| 5,004,435 A | 4/1991 | Jammet |
| 5,014,913 A | 5/1991 | Hoyt et al. |
| 5,015,442 A | 5/1991 | Hirai |
| 5,029,729 A | 7/1991 | Madsen et al. |
| 5,038,394 A | 8/1991 | Hasegawa et al. |
| 5,050,798 A | 9/1991 | Sullivan |
| 5,106,317 A | 4/1992 | Taylor |
| 5,111,477 A | 5/1992 | Muderlak |
| 5,115,975 A | 5/1992 | Shilling |
| 5,121,881 A | 6/1992 | Lembeck |
| 5,126,078 A | 6/1992 | Steiner et al. |
| 5,136,684 A | 8/1992 | Lonker et al. |
| 5,147,582 A | 9/1992 | Holzner, Sr. et al. |
| 5,148,984 A | 9/1992 | Bryson, Jr. et al. |
| 5,175,791 A | 12/1992 | Muderlak et al. |
| 5,196,171 A | 3/1993 | Peltier |
| 5,201,025 A | 4/1993 | Landesberg |
| 5,217,696 A | 6/1993 | Wolverton et al. |
| 5,220,636 A | 6/1993 | Chang |
| 5,222,186 A | 6/1993 | Schimanski et al. |
| 5,223,182 A | 6/1993 | Steiner et al. |
| 5,233,680 A | 8/1993 | Fussell |
| 5,239,610 A | 8/1993 | Shao |
| 5,240,426 A | 8/1993 | Barla |
| 5,285,014 A | 2/1994 | Gilchrist |
| 5,290,546 A | 3/1994 | Hasegawa et al. |
| 5,295,845 A | 3/1994 | Changxing |
| 5,314,669 A | 5/1994 | Hamilton |
| 5,320,542 A | 6/1994 | Cheng |
| 5,339,065 A | 8/1994 | Slenker |
| 5,342,584 A | 8/1994 | Fritz et al. |
| 5,373,581 A | 12/1994 | Smith |
| 5,375,728 A | 12/1994 | West |
| 5,376,338 A | 12/1994 | Zlotnik |
| 5,382,410 A | 1/1995 | Peltier |
| D355,251 S | 2/1995 | Paulovich et al. |
| 5,394,506 A | 2/1995 | Stein et al. |
| 5,402,517 A | 3/1995 | Gillett et al. |
| D357,330 S | 4/1995 | Wong et al. |
| 5,431,859 A | 7/1995 | Tobin |
| 5,431,885 A | 7/1995 | Zlotnik et al. |
| 5,445,802 A | 8/1995 | Wendelken |
| 5,465,198 A | 11/1995 | Kellogg |
| 5,480,591 A | 1/1996 | Lagneaux et al. |
| 5,481,442 A | 1/1996 | Wiltshire et al. |
| 5,484,086 A | 1/1996 | Pu |
| 5,498,397 A | 3/1996 | Horng |
| 5,521,357 A | 5/1996 | Lock et al. |
| 5,522,008 A | 5/1996 | Bernard |
| 5,547,616 A | 8/1996 | Dancs et al. |
| 5,556,192 A | 9/1996 | Wang |
| 5,567,361 A | 10/1996 | Harper |
| 5,574,821 A | 11/1996 | Babasade |
| 5,575,992 A | 11/1996 | Kunze |
| 5,577,156 A | 11/1996 | Costello |
| 5,591,395 A | 1/1997 | Schroeder et al. |
| 5,624,230 A | 4/1997 | Taylor et al. |
| 5,634,806 A | 6/1997 | Hahn |
| 5,647,052 A | 7/1997 | Patel et al. |
| 5,647,053 A | 7/1997 | Schroeder et al. |
| 5,651,942 A | 7/1997 | Christinsen |
| 5,662,835 A | 9/1997 | Collingwood |
| 5,664,958 A | 9/1997 | Chadwick et al. |
| 5,700,430 A | 12/1997 | Bonnema et al. |
| 5,735,460 A | 4/1998 | Eisenbraun |

| | | |
|---|---|---|
| 5,749,520 A | 5/1998 | Martin et al. |
| 5,750,498 A | 5/1998 | Soeda et al. |
| 5,765,751 A | 6/1998 | Joshi |
| 5,788,155 A | 8/1998 | Martin et al. |
| 5,788,931 A | 8/1998 | Munoz Quintana |
| 5,796,914 A | 8/1998 | Gatzemeyer et al. |
| 5,805,768 A | 9/1998 | Schwartz et al. |
| 5,810,265 A | 9/1998 | Cornelius et al. |
| 5,813,873 A | 9/1998 | McBain et al. |
| 5,832,648 A | 11/1998 | Malone |
| 5,873,529 A | 2/1999 | Johnson |
| 5,875,968 A | 3/1999 | Miller et al. |
| 5,884,808 A | 3/1999 | Muderlak et al. |
| 5,899,381 A | 5/1999 | Gordon et al. |
| 5,903,710 A | 5/1999 | Wefler et al. |
| 5,926,614 A | 7/1999 | Steinel |
| 5,928,605 A | 7/1999 | Bonnema et al. |
| 5,932,204 A | 8/1999 | Joshi |
| 5,937,140 A | 8/1999 | Leonard et al. |
| 5,940,577 A | 8/1999 | Steinel |
| 5,944,223 A | 8/1999 | Klima et al. |
| 5,945,094 A | 8/1999 | Martin et al. |
| 5,955,701 A | 9/1999 | Schockner et al. |
| 5,957,701 A | 9/1999 | McMillin |
| 5,970,643 A | 10/1999 | Gawel, Jr. |
| 5,976,503 A | 11/1999 | Martin et al. |
| 5,998,735 A | 12/1999 | Patterson, Jr. |
| 6,021,254 A | 2/2000 | Hunter |
| 6,031,967 A | 2/2000 | Flashinski et al. |
| 6,032,930 A | 3/2000 | Calino |
| 6,036,536 A | 3/2000 | Chiu |
| 6,044,202 A | 3/2000 | Junkel |
| 6,045,374 A | 4/2000 | Candeloro |
| 6,050,551 A | 4/2000 | Anderson |
| 6,051,788 A | 4/2000 | Nichols |
| 6,078,728 A | 6/2000 | O'Rourke et al. |
| 6,085,026 A | 7/2000 | Hammons et al. |
| 6,097,881 A | 8/2000 | DeWitt et al. |
| 6,099,137 A | 8/2000 | McCormick et al. |
| 6,101,315 A | 8/2000 | Steinel, Jr. |
| 6,104,866 A | 8/2000 | DeWitt et al. |
| 6,104,867 A | 8/2000 | Stathakis et al. |
| D430,659 S | 9/2000 | Zaragoza et al. |
| 6,123,935 A | 9/2000 | Wefler et al. |
| 6,141,496 A | 10/2000 | Sundberg et al. |
| 6,148,143 A | 11/2000 | Steinel, Jr. |
| 6,156,088 A | 12/2000 | Cardarelli |
| 6,197,262 B1 | 3/2001 | Del Ben |
| 6,197,263 B1 | 3/2001 | Blount |
| 6,227,118 B1 | 5/2001 | Nance |
| 6,236,807 B1 | 5/2001 | Ruffolo et al. |
| 6,249,645 B1 | 6/2001 | Smith |
| 6,254,065 B1 | 7/2001 | Ehrensperger et al. |
| 6,264,548 B1 | 7/2001 | Payne, Jr. et al. |
| 6,269,979 B1 | 8/2001 | Dumont |
| 6,270,720 B1 | 8/2001 | Mandish |
| 6,275,651 B1 | 8/2001 | Voit |
| 6,278,840 B1 | 8/2001 | Basaganas Millan |
| 6,285,830 B1 | 9/2001 | Basaganas Millan |
| 6,289,176 B1 | 9/2001 | Martter et al. |
| 6,302,559 B1 | 10/2001 | Warren |
| 6,315,959 B2 | 11/2001 | Mandish |
| 6,328,791 B1 | 12/2001 | Pillion et al. |
| 6,342,676 B1 | 1/2002 | Ha |
| 6,349,168 B1 | 2/2002 | Jaworski |
| 6,352,210 B1 | 3/2002 | Requejo |
| 6,354,513 B1 | 3/2002 | Basaganas Millan |
| 6,361,752 B1 | 3/2002 | Demarest et al. |
| 6,364,673 B1 | 4/2002 | Lee |
| 6,368,564 B1 | 4/2002 | Smith |
| 6,371,815 B1 | 4/2002 | Wetzel et al. |
| 6,374,044 B1 | 4/2002 | Freidel |
| 6,374,045 B2 | 4/2002 | Basaganas Millan |
| 6,381,408 B1 | 4/2002 | Jaworski et al. |
| 6,603,924 B2 | 8/2003 | Brown et al. |
| 6,714,725 B2 | 3/2004 | Grone et al. |
| 2001/0031225 A1 | 10/2001 | Mandish |
| 2001/0053283 A1 | 12/2001 | Levine et al. |
| 2002/0144992 A1 | 10/2002 | Vieira |
| 2003/0138241 A1 | 7/2003 | Ambrosi et al. |

OTHER PUBLICATIONS

PCT International Search Report issued Oct. 7, 2003 for International Application No. PCT/US03/04082, International Filing Date Feb. 12, 2003, 8 pages.

PCT International Search Report issued Dec. 16, 2003 for International Application No. PCT/US03/25244, International Filing Date Aug. 13, 2003, 3 pages.

PCT International Search Report issued Dec. 16, 2003 for International Application No. PCT/US03/25246, International Filing Date Aug. 13, 2003, 3 pages.

PCT International Search Report issued Dec. 19, 2003 for International Application No. PCT/US03/25243, International Filing Date Aug. 13, 2003, 4 pages.

Brochure–"Decora Devices," by Leviton, date unknown, Section A, pps. A1–A36.

PCT Written Opinion issued Jul. 15, 2004 for International Application No. PCT/US03/25244, International Filing Date Aug. 13, 2003, 5 pages.

* cited by examiner

FIG.8

METHODS AND APPARATUS FOR A DISCRETE VAPOR-DISPENSING DEVICE

CROSS-REFERENCE TO RELATED APPLICATIONS

This application is a continuation-in-part of U.S. patent application Ser. No. 10/222,079 entitled "Methods and Apparatus for a Discrete Vapor-Dispensing Device" filed Aug. 16, 2002 which is incorporated herein by reference.

BACKGROUND OF THE INVENTION

This invention relates, generally, to vapor-dispensing devices and, in particular, to a vapor-dispensing device which integrates with a receptacle in a discrete manner.

TECHNICAL FIELD

It is often convenient to use an available receptacle, for example, a conventional household electrical outlet, as a source of electrical power for systems configured to perform some type of environment-altering task. Known environment-altering systems include, for example, plug-in air-fresheners, vapor-dispensing devices, plug-in ultrasonic pest control devices, night-lights, ionizers, and the like.

Due to the location and accessibility of conventional wall outlets, and the size and shape of known vapor-dispensing devices, it is common for such devices to be relatively conspicuous when plugged into a wall outlet. In the case of household plug-in air-fresheners, for example, this may give rise to unfortunate conclusions in the minds of visitors with respect to the overall quality of air in the home.

In some instances it may therefore be desirable to enhance the extent to which vapor-dispensing devices integrate or blend in with their environment. The level of discreetness is generally related to a device's overall geometry and the manner in which the device contacts the wall and/or receptacle to which it is connected.

In addition to this aesthetic discreetness, it would also be advantageous to provided an environment-altering apparatus with enhanced functional discreetness. That is, there is a need for vapor-dispensing devices which do not eliminate, reduce, or otherwise alter a user's access to the functional features of the receptacle. In the case of plug-in air-fresheners, for example, it would be advantageous to provide an air-freshener wherein access to all or most of the receptacle's outlets are substantially maintained.

SUMMARY OF THE INVENTION

In general, the present invention provides a vapor-dispensing device or other environment-altering apparatus configured to integrate with its environment in a discreet manner. The apparatus may accomplish this discreetness in a number of ways—for example, by blending in with one or more components of the environment (e.g., a wall or other surface), by covering or otherwise occluding all or a portion of the receptacle, and/or by appearing to be something other than an environment-altering device.

One way the environment-altering device may blend in with its environment is by including a housing configured such that a cross-section orthogonal to and through the perimeter of the housing defines a blending contour from the front surface to the wall outside the perimeter of the electrical receptacle.

Another way the device may accomplish blending with its environment is by exhibiting a particular color, texture, and/or geometry which matches or is otherwise thematically consistent with the environment in which the device is to be placed.

Yet another way the environment-altering device may blend in with its environment is by making contact with a wall or other surface in the vicinity of the receptacle. In one embodiment, for example, the device includes a housing having at least two antipodal points on the perimeter of the housing that make contact with the wall outside the perimeter of the receptacle faceplate when the device is connected to the receptacle.

In accordance with a further aspect of the present invention, a vapor-dispensing device blends into its environment by exhibiting a low profile normalized in terms of an inter-outlet dimension or one or more other suitable dimensions.

The environment-altering device may also be configured to entirely or partially cover the electrical receptacle in a number of different ways. In accordance with a one embodiment of the present invention, for example, the device may include a housing whose perimeter substantially encompasses the perimeter of a electrical receptacle's faceplate when the vapor-dispensing device is connected to the electrical receptacle.

In accordance with a further aspect of the present invention, a vapor-dispensing device covers the receptacle by including a housing whose aspect ratio is substantially similar to the aspect ratio of a receptacle faceplate, and whose center is substantially coincident with the center of the faceplate.

In accordance with another aspect of the present invention, discreetness is achieved by configuring the environment-altering device such that it appears to be something other than an environment-altering device.

In accordance with one embodiment of the present invention, for example, an environment-altering apparatus is configured to mimic an electrical receptacle having an outlet pattern. The environment-altering apparatus has a front surface which includes an outlet pattern substantially corresponding to the outlet pattern of the electrical receptacle, and a plug configured to interface with the electrical receptacle. A device configured to modify one or more attributes of the environment is interposed between the front surface and plug pattern. These attributes include, for example, aromatic vapor density, insecticide vapor density, ambient light intensity, ionic air content, ultrasonic frequency intensity, and the like.

BRIEF DESCRIPTION OF THE DRAWINGS

The subject invention will hereinafter be described in conjunction with the appended drawing figures, wherein like numerals denote like elements, and:

FIG. 8 illustrates a variety of exemplary receptacle and outlet configurations;

DETAILED DESCRIPTION

Systems and methods in accordance with the present invention generally provide a vapor-dispensing device or other environment-altering apparatus configured to integrate with its environment in a discreet manner, e.g., by blending in with one or more components of the environment, by covering or otherwise occluding all or a portion of the receptacle, and/or by appearing to be something other than an environment-altering device.

Figure 1:
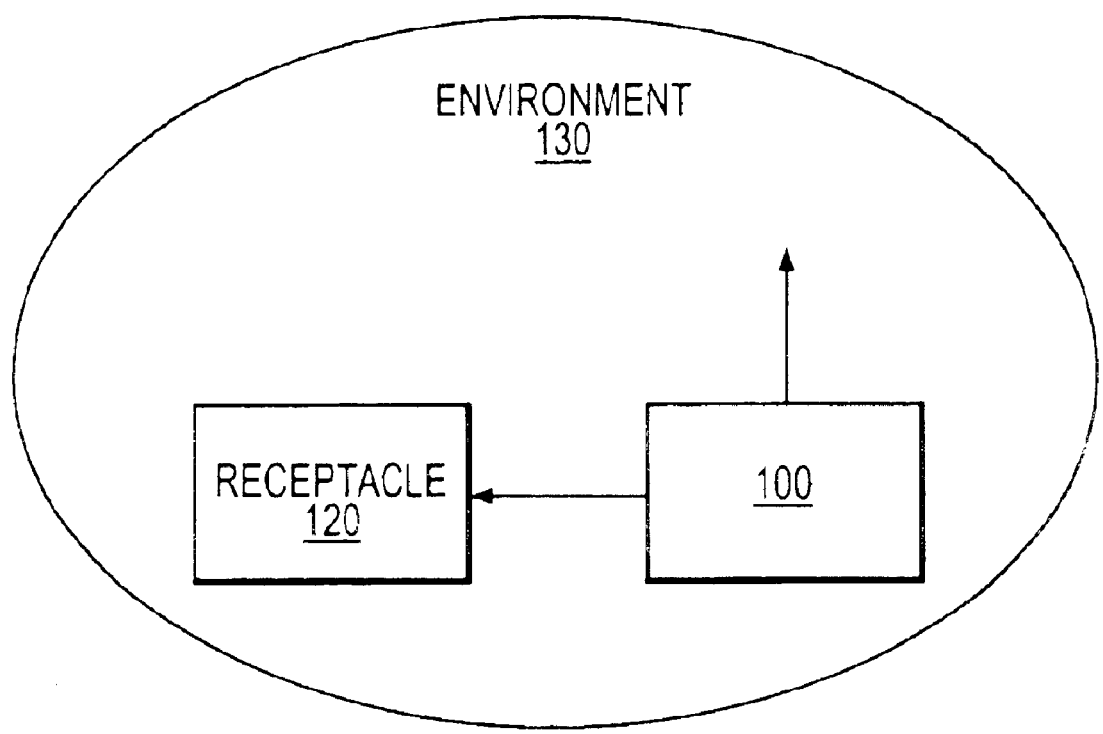
FIG. 1 is a schematic overview of a system providing a context in which the present invention may be practiced.

Referring to FIG. 1, an environmental-altering apparatus 100 in accordance with the present invention generally interfaces with a receptacle 120 within an environment 130. Environmental-altering apparatus 100 comprises any suitable component or combination of components configured to alter environment 130 in some manner, e.g., by altering its aromatic vapor density, dispensing an insecticide, providing a light source, ionizing the ambient air, and/or providing a source of ultrasonic sound. In this regard, the phrase "vapor-dispensing device" may, without loss of generality, be used herein to refer to the environment-altering apparatus. Those skilled in the art will recognize that the present invention is not so limited.

Environment 130 corresponds to any defined space, whether open or enclosed by one or more surfaces, walls, ceilings, floors, or other solid or fictitious boundaries, which receives the evaporated material. For example, environment 130 may correspond to a residential room (bedroom, bathroom, kitchen, etc.), commercial space (factory floor, office cubicles, etc.), automotive enclosure (car, truck, recreational-vehicle), airline compartment, or any other space in which it is desirable to deliver a vapor.

In accordance with one embodiment of the present invention, an environment-altering apparatus is configured to give the appearance that it is something other than an environment-altering apparatus. For example, the environment-altering apparatus may be configured to mimic an electrical receptacle having an outlet pattern. In this embodiment, the environment-altering apparatus has a front surface which includes an outlet pattern substantially corresponding to the outlet pattern of the receptacle, and a plug configured to interface with the electrical receptacle.

Figure 2:
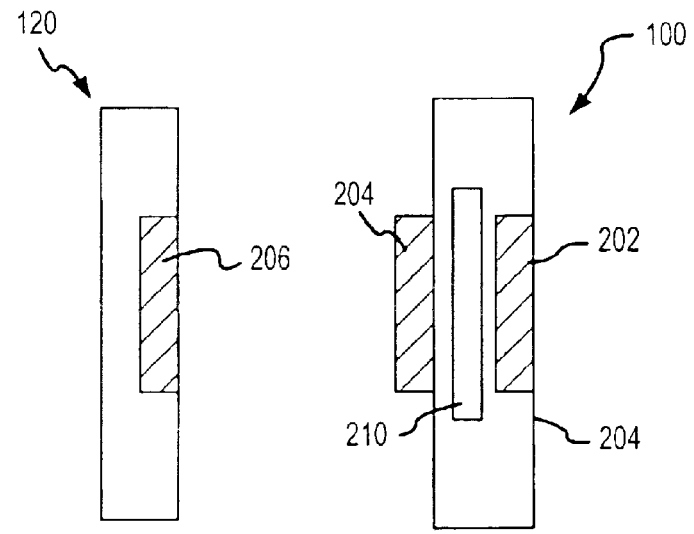
FIG. 2 shows a schematic side view of a vapor-dispensing device and receptacle in accordance with the present invention.

For example, referring now to FIG. 2, a vapor dispensing device 100 interfaces with a receptacle 120 through one or more plugs (or other interface structures) 204 corresponding to an outlet pattern 206. Vapor dispensing device 100 has a front surface 204 (which may or may not be planar) that includes an outlet pattern 202 which substantially corresponds to outlet pattern 206 of receptacle 120. Thus, vapor dispensing device 100 is generally configured to removeably attach to receptacle 120.

A device 210 configured to modify one or more attributes of the environment is suitably interposed between (and/or to the side of) the front surface 204 and plug pattern 204. Environmental attributes modified by device 210 include, for example, aromatic vapor density, insecticide vapor density, ambient light intensity, ionic air content, ultrasonic frequency intensity, and the like. In an embodiment wherein device 210 corresponds to a fragrance delivery device, it may also include one or more components (e.g., wicks, capillary tubes, and the like) which provide a means for at transporting volatizable material from one location to another (e.g., from a reservoir to a evaporation pad or eminator), and/or one or more components (eminator pads, secondary wicks, and the like) which provide a surface or surfaces from which the transported material undergoes mass transfer or evaporation to environment 120.

In an embodiment wherein receptacle 120 corresponds to an electrical power outlet, it is advantageous to utilize this power source to provide any electrical functionality required by the fragrance delivery device. For example, fragrance delivery device may include one or more eminators or heating elements designed to control the rate at which the volatizable material evaporates into the environment. In such a case, delivery device 210 may include various terminals, wires, conductive traces, plugs, and other such components facilitating interface and power delivery to receptacle 120. In a particularly preferred embodiment, for example, delivery device 210 includes a resistive heating element that is thermally coupled to an eminator pad or wick which communicates with a volatizable material.

Figures 3, 4:
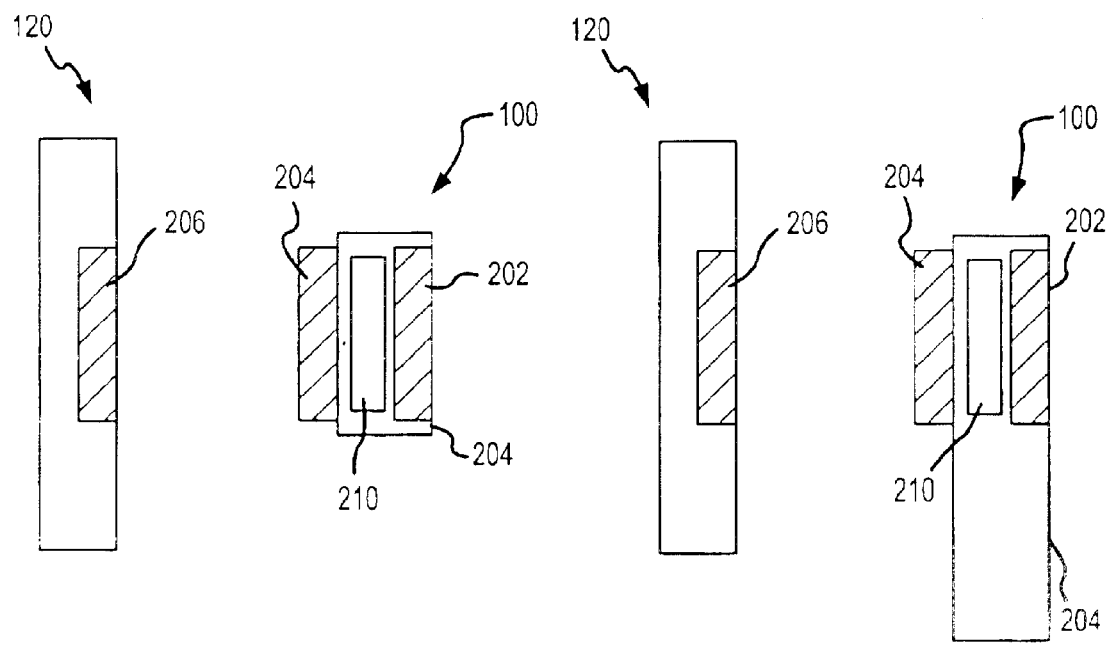
FIG. 3 shows a schematic side view of a vapor-dispensing device and receptacle in accordance with another embodiment of the present invention.
FIG. 4 shows a schematic side view of a vapor-dispensing device and receptacle in accordance with yet another embodiment of the present invention.

Although the vapor dispensing device 100 of FIG. 2 is illustrated as generally rectilinear in cross-section, it may in fact include any number of discrete or integrated housings having any arbitrary shape. Furthermore, in accordance with this embodiment, it is not necessary for vapor dispensing device 100 to exhibit a geometry which is similar in size or shape to that of receptacle 120 or any face-plates provided in conjunction with receptacle 120. That is, as shown in FIG. 3, a discreet vapor dispensing device 100 may actually be smaller than receptacle 120 (e.g., on the order of the size of plug pattern 204). Similarly, as shown in FIG. 4, vapor-dispensing device may be asymmetrical with respect to receptacle 120 and/or any plug pattern 206 provided in receptacle 120. As shown in FIG. 4, for example, the lower boundary of front face 204 may extend below (or above) receptacle 120.

Figure 5:
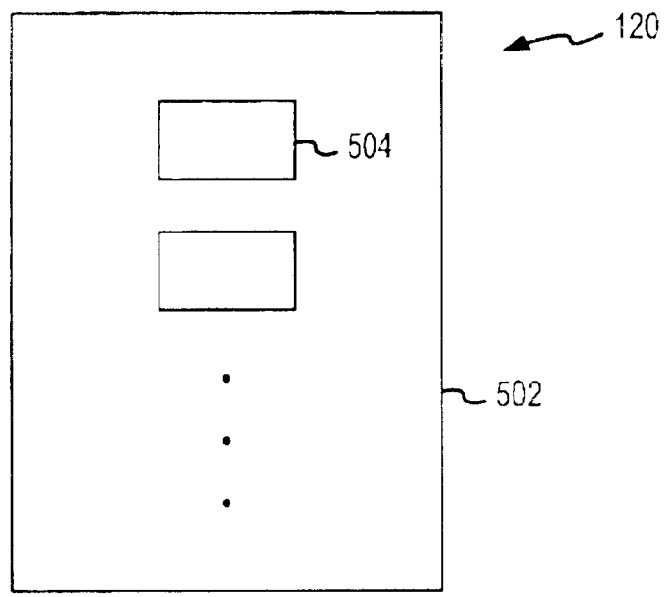
FIG. 5 is a schematic front view of an exemplary receptacle having a number of outlets.
Figure 6:
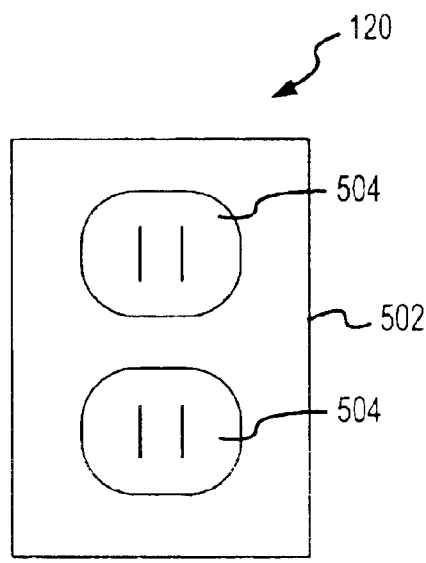
FIG. 6 depicts a conventional dual-outlet receptacle.
Figure 7:
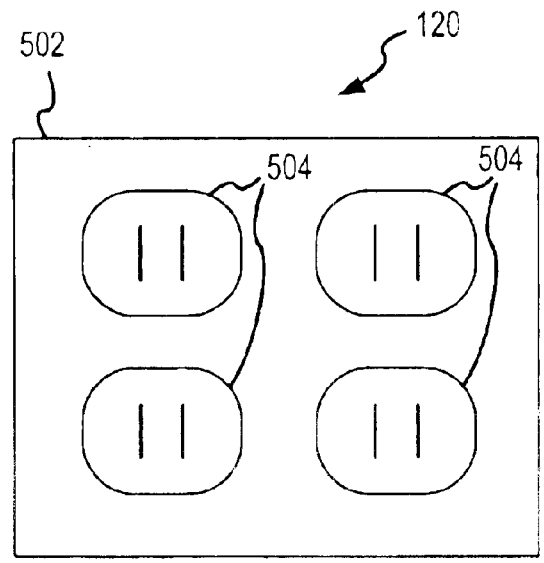
FIG. 7 depicts a conventional quad-outlet receptacle.
Figure 8:
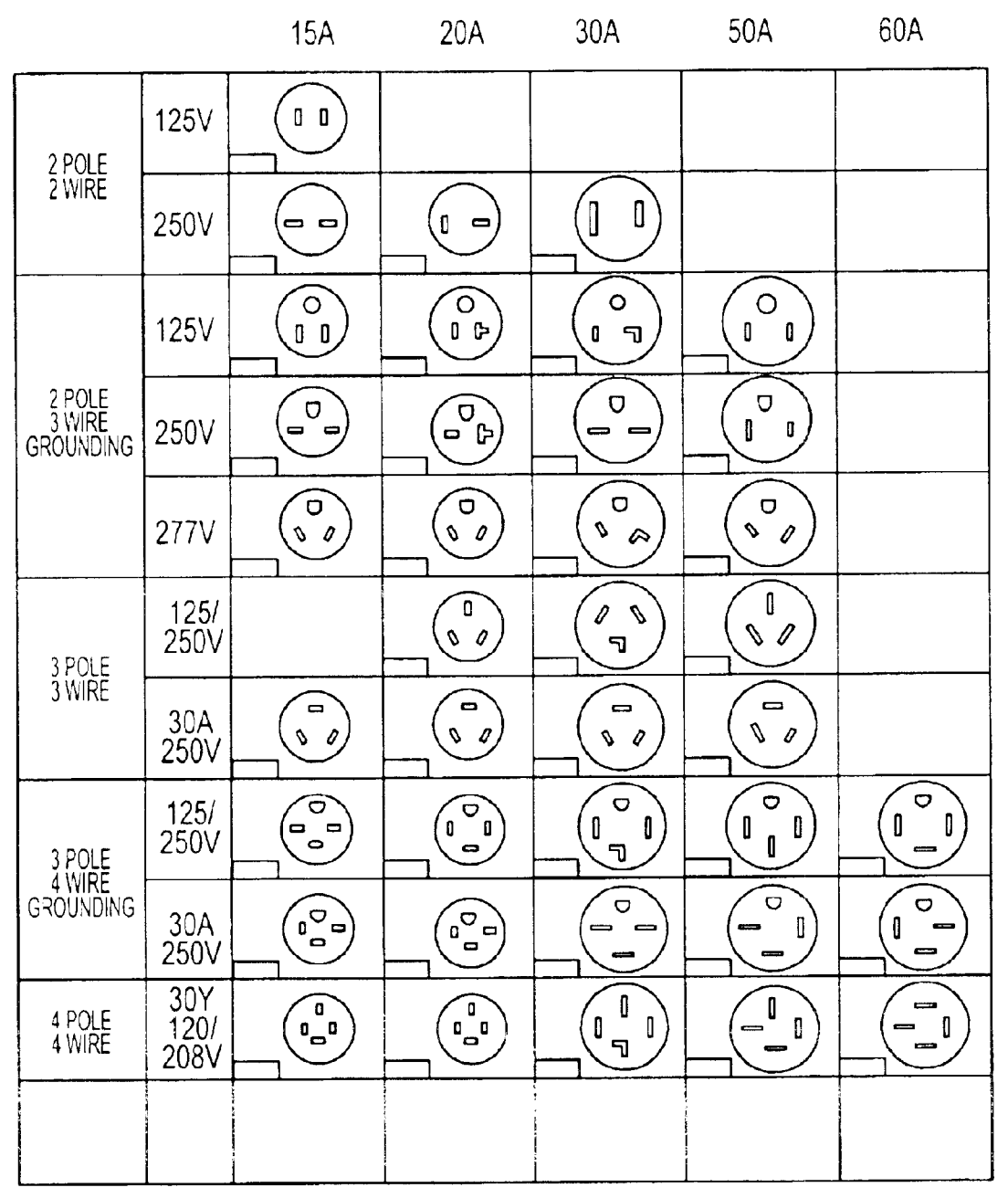

FIG. 5 shows a general configuration for receptacle 120 which includes an outer boundary and/or faceplate 502 along with one or more outlets 504. Outlets 504 may exhibit any suitable shape, and may include any suitable combination of male, female, or other connection types. For example, referring now to FIG. 6, receptacle 120 may consist of a conventional dual-outlet power receptacle including a pair of two-prong outlets 504 and a faceplate 502. Similarly, as shown in FIG. 7, receptacle 120 may consist of a conventional quad-outlet power receptacle including four two-prong outlets 504 and a faceplate 502. FIG. 8 presents a matrix of additional standard receptacle designs with which the present invention may be employed. Note also that the present invention may be used in connection with ground-fault interrupt (GFI) electrical outlets.

It will be appreciated that the present invention is not limited to electrical receptacles. Indeed, receptacle 120 may comprise any suitable structure configured to provide electricity, data, or any other power and/or information source to vapor-dispensing device 100 through a suitable interface. For example, suitable receptacles include RJ-11 and RJ-45 jacks used in connection with high-speed data transfer (and analog telephone communication), co-axial connectors used in connection with electrical and optical cable networks, and any other receptacle design now known or developed in the future.

Notwithstanding the nature of receptacle 120—i.e., whether and to what extent receptacle 120 is configured to supply electrical current—delivery device 210 may be passive, active, or selectably switched between active and passive modes. The term "passive" in this context, as applied to delivery devices, refers to those devices which substantially depend upon ambient conditions to deliver a fragrance or otherwise give rise to a modification of the environment. Such ambient conditions include, for example, ambient thermal conditions (e.g., wall surface temperature and air temperature) and ambient air flow, (e.g., air flow resulting from free convection as well as the movement (if any) of fans, individuals, and other entities within the environment). The term "active" in this context refers to devices that are not passive, e.g., devices which employ integrated fans, heating elements, and other such devices.

In the event that delivery device 210 is an active device, any power source required by the device may be intrinsic to receptacle 120, e.g., the 120 V source of a standard wall outlet, or extrinsic to receptacle 120, e.g., supplied by a battery, solar cell, or other such device incorporated into or otherwise associated with delivery device 210. Alternatively, power may be supplied by a combination of intrinsic and extrinsic sources and/or may be incorporated into a refill component, described in further detail below.

In order to achieve the goal of appearing to be something other than a vapor-dispensing device, the device may be designed to mimic not only an electrical receptacle, but any number of other objects which might typically appear in the target environment. For example, the vapor-dispensing device might be configured to mimic a wall switch, a multi-outlet power strip, a night-light, or any other suitable object.

As mentioned above, discreetness of the environment-altering device may also be achieved by configuring the device such that it blends in with its environment. This blending may be accomplished, for example, by including a housing configured such that a cross-section orthogonal to and through the perimeter of the housing defines a blending contour from the front surface to the wall outside the perimeter of the electrical receptacle.

Figure 9:
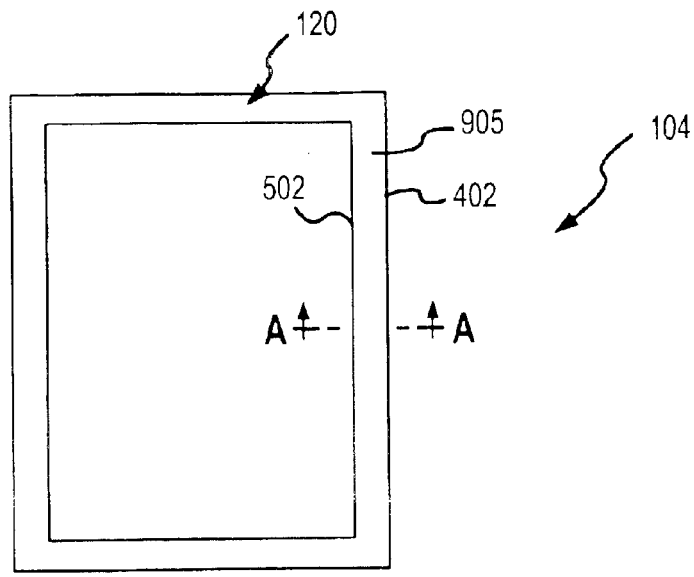
FIG. 9 schematically illustrates an exemplary vapor dispensing device.

Referring to FIG. 9, for example, a receptacle 120 includes a faceplate 502, which may or may not be rectangular as illustrated. Faceplate 502 generally fits against or flush with a wall 904. A housing 904 has a perimeter 902 (which need not be rectangular, and need not correspond to the shape of faceplate 502) that is characterized by a cross-section 'A' as shown, wherein the cross-section defines a blending-contour with respect to wall 904, thus providing added discreetness. More particularly, referring to FIG. 9 in connection with the six example cross-sections illustrated in FIG. 10, a cross-section 1000 near the perimeter 902 of housing 905 forms a blending-contour between the front 1002 and wall 904. In general, blending contour 1000 forms a continuous (but not necessarily smooth or differentiable) curve extending from the front 1002 of housing 905 to a terminus 1004 near or in contact with wall 904.

Figure 10:
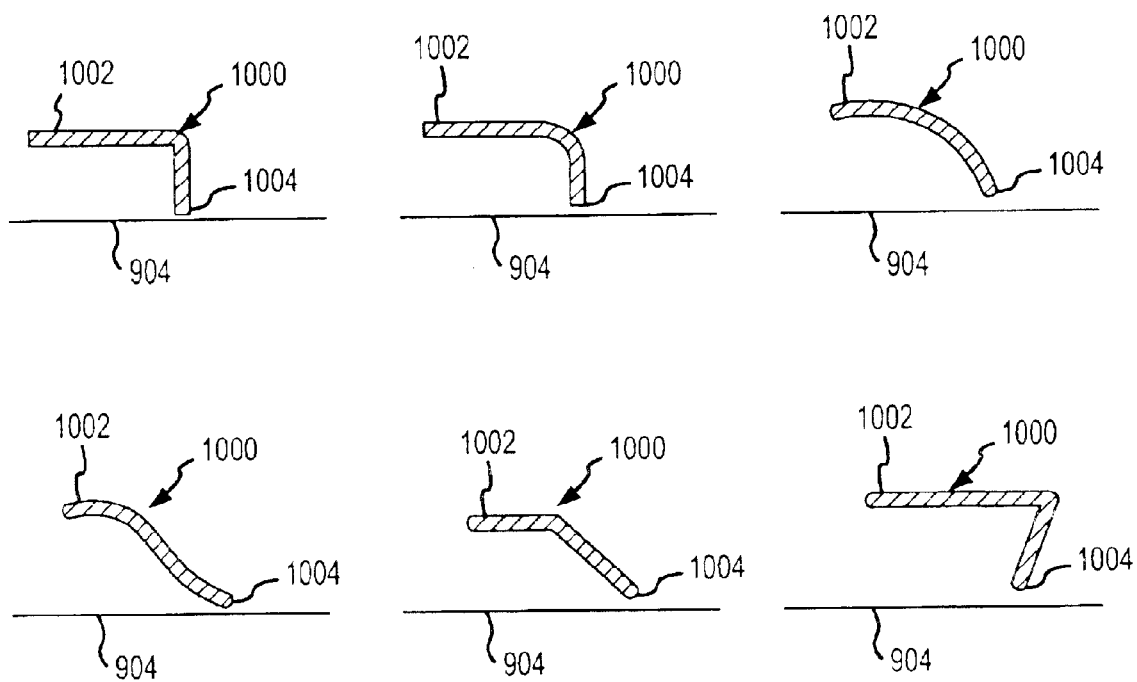
FIG. 10 depicts various cross-section diagrams defining blending contours.
Figure 11A:
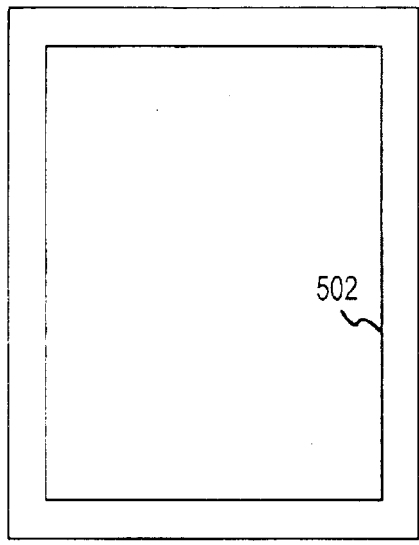
FIG. 11 depicts various configurations of vapor-dispensing device geometries with respect to a receptacle.
Figure 11B:
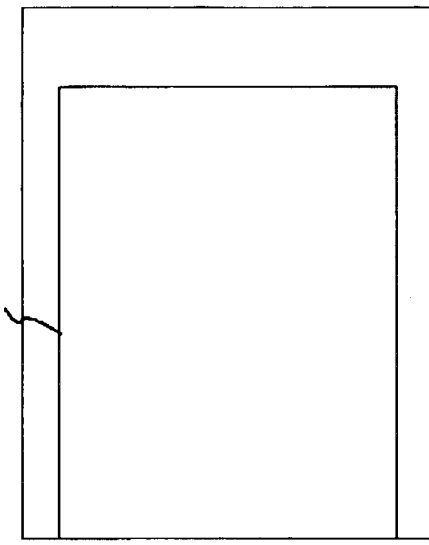
Figure 11C:
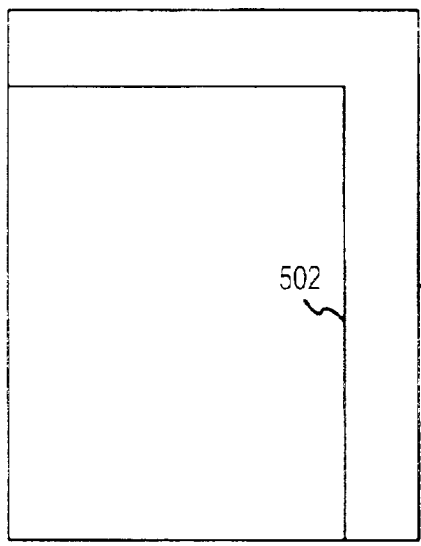
Figure 11D:
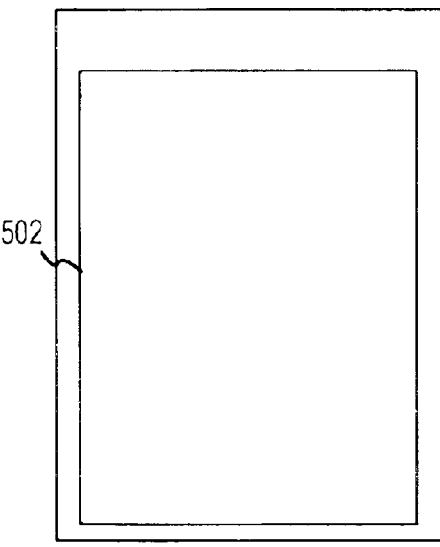

It will be appreciated that the exemplary shapes shown in FIG. 10 do not exhaust the range of blending-contour shapes that may be used in accordance with the present invention.

In accordance with a further aspect of the present invention, a vapor-dispensing device blends in with its environment by including a housing wherein at least two antipodal points on the perimeter of the housing make contact with the wall outside the perimeter of the receptacle faceplate when the device is connected to the receptacle.

Figure 13:
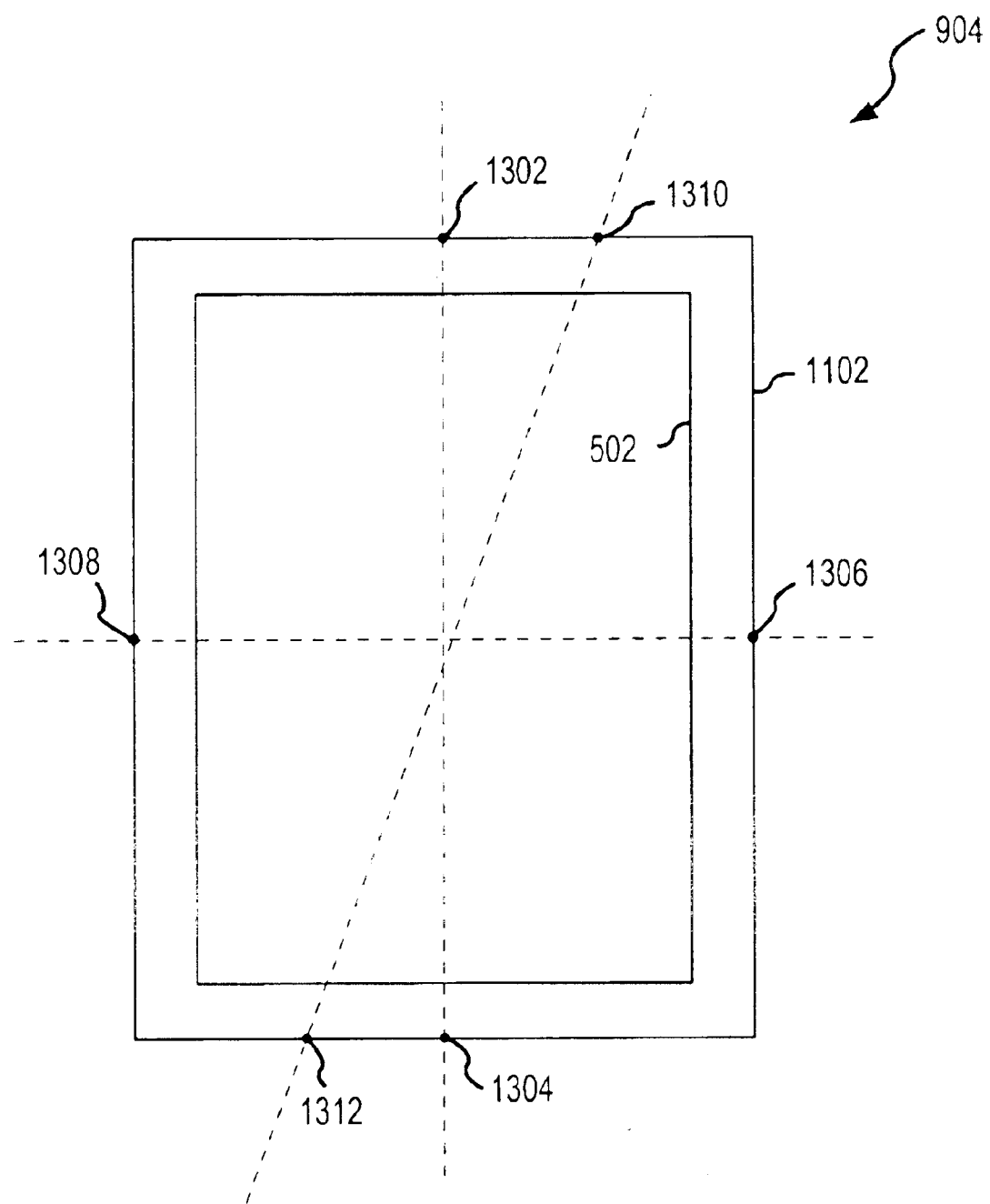
FIG. 13 depicts exemplary vapor-dispensing device symmetries.

Referring to FIG. 13, housing perimeter 1102 is configured such that at least two points on opposite sides of housing perimeter 1102 make contact with a wall 904 outside of faceplate perimeter 502. For example, housing perimeter 1102 may make contact with wall 904 at one or more of the following pairs of points: points 1302 and 1304; points 1306 and 1308; and points 1310 and 1312. The word "point" is used in the sense of a location, and need not correspond to a small circular contact point; indeed, any arbitrary contact region (or closely situated regions) may be considered a "point" as that term is used in connection with this embodiment.

Figure 14:
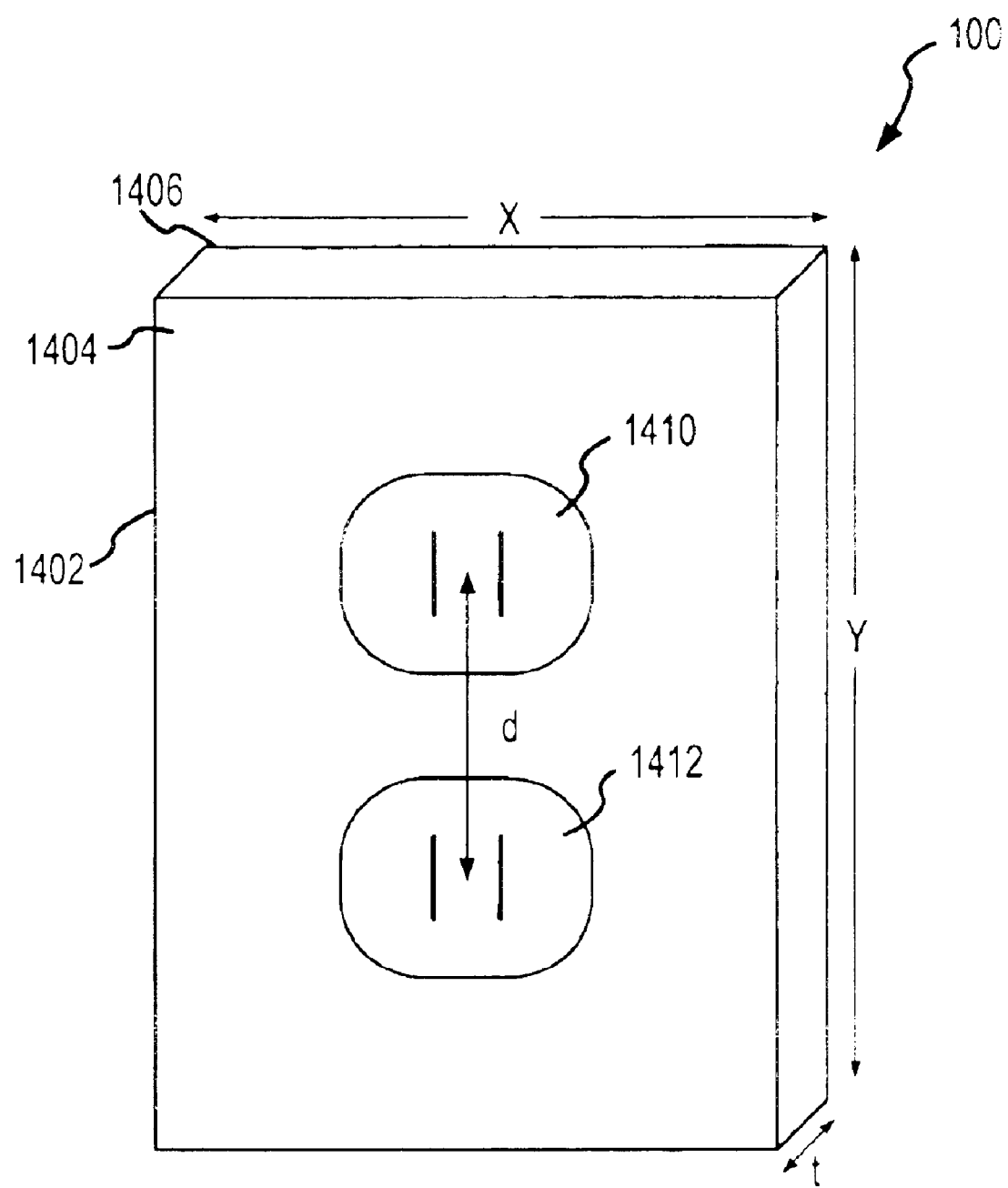
FIG. 14 is an isometric view showing exemplary vapor-dispensing device geometries.

In accordance with a further aspect of the present invention, a vapor-dispensing device has low-profile dimensions. More particularly, referring now to FIG. 14, an exemplary vapor-dispensing device 100 includes a housing 1402 having a front surface 1404 and a back surface 1406 separated by a thickness t, wherein back surface 1406 has a minor axis dimension x and a major axis dimension y. A first device outlet 1410 and a second device outlet 1412 are provided on the front surface 1404 of housing 1402. The device outlets (1410 and 1412) are separated by an inter-outlet distance d; wherein: x/d is between approximately 2.0 and 2.5, preferably about 2.125, y/d is between approximately 3.0 and 3.5, preferably about 3.25, and t/d is between approximately 0.5 and 1.0, preferably about 0.625 In accordance with yet a further aspect of the present invention, the thickness t is less than approximately 20% of the major axis dimension y.

In order to achieve the goal of blending in with the environment, any number of other attributes of the device may be designed to match or be thematically consistent with one or more attributes of the environment. For example, the device's color, texture, and/or geometry may be selected to better blend in with the wall, furniture, or other components of the environment.

Discreetness of the environment-altering device may also be achieved by configuring the device such that it covers all or a portion of the receptacle. In accordance with one aspect of the present invention, for example, a vapor-dispensing device substantially covers the receptacle by including a housing whose perimeter substantially encompasses the perimeter of a electrical receptacle's faceplate when the vapor-dispensing device is connected to the electrical receptacle.

More particularly, referring to the four exemplary configurations shown in FIG. 11, a faceplate perimeter 502 (or, alternatively, receptacle perimeter) is substantially encompassed by the housing perimeter 1102. That is, housing perimeter 1102 may fully encompass faceplate perimeter 502 such that all points on perimeter 502 fall within the area defined by housing perimeter 1102 (as shown in FIGS. 11(*a*) and 11(*b*)) or so that a portion of faceplate perimeter 502 lies at the border of (or indeed, slightly outside of ) housing perimeter 1102 (as shown in FIGS. 11(*b*) and 11(*c*)). While the illustrated faceplates and housings shown in FIG. 11 are generally rectangular and generally correspond to each other, the faceplates and housings may have any variety of shapes, and it is not necessary for the shapes to generally correspond to each other. For example, faceplate perimeter 502 may be rectangular while housing perimeter 1102 is circular or elliptical. In accordance with a further aspect of the present invention, a vapor-dispensing device includes a housing whose aspect ratio is substantially similar to the aspect ratio of a receptacle faceplate, and whose center is substantially coincident with the center of the faceplate.

Delivery device 210 suitably includes one or more removeably attached refill components. That is, referring to FIGS. 15A–15C, it may be advantageous for delivery device 210 to include components that are integral to the delivery device itself as well as one or more refill components 1502 (or simply "refills") that can be replaced by the user. In the event delivery device 210 is an air freshener device, for example, a depleted refill component 1502 may removed from device 210 and replaced by a new refill containing fragrant oil, wax, gel, or the like. The refill suitably includes a refill body and a volatizable material provided therein.

In accordance with one aspect of the present invention, a refill component is provided which allows vapor-dispensing device to mimic an electrical receptacle. For example, a refill component comprising a refill body having a volatizable material provided therein may be configured to be inserted behind the front surface of the device such that it is substantially concealed by the front surface. In accordance with one aspect of the present invention, the refill has a perimeter that is encompassed by the perimeter of the housing.

Figures 15A, 15B, 15C:
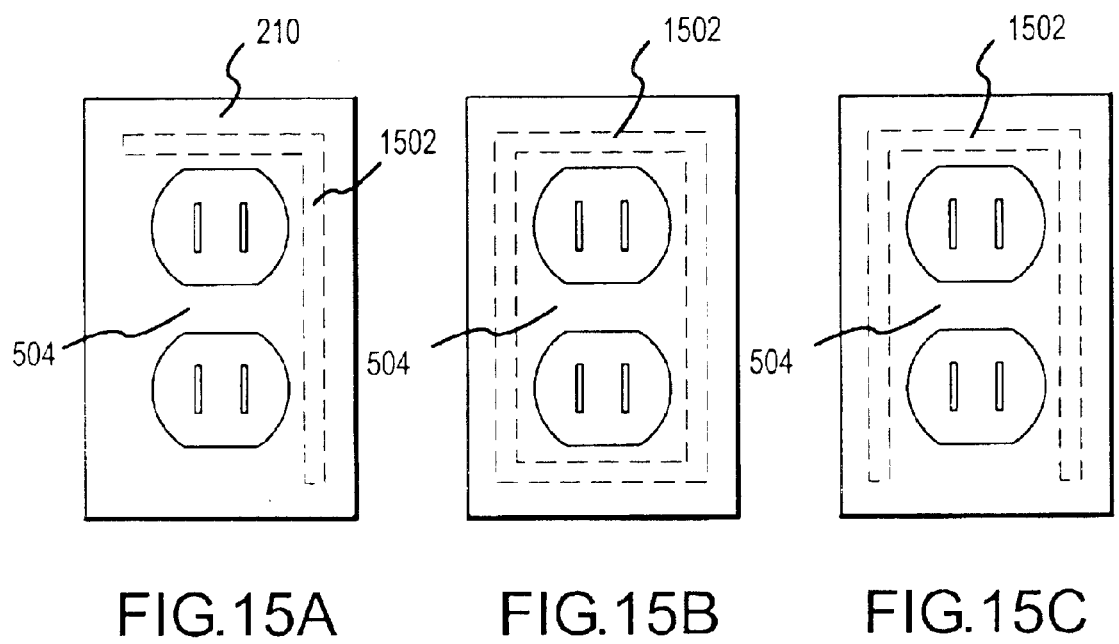
FIGS. 15A–15C depict various refill geometries in accordance with one aspect of the present invention.

In accordance with another aspect of the present invention, the refill is configured such that it does not significantly obstruct the receptacle's outlet pattern 504. In one embodiment, for example, this is accomplished by providing a refill component 1502 that at least partially surrounds one or more outlets on the receptacle (variously shown in FIGS. 15A–15C). In the event that the delivery device is used in connection with a standard electrical receptacle, it is desirable for refill 1502 to encompass two or more sides of the outlet pattern (FIG. 15A). To the extent that it is advantageous to supply the greatest possible volume of volatizable material, the refill may be configured as a rectangular ring that completely surrounds the outlet pattern 504 (FIG. 15B). Alternatively, the refill may be configured in a 'U' shape to allow refill 1502 to be slideably removed from the device (FIG. 15C).

Figure 12:
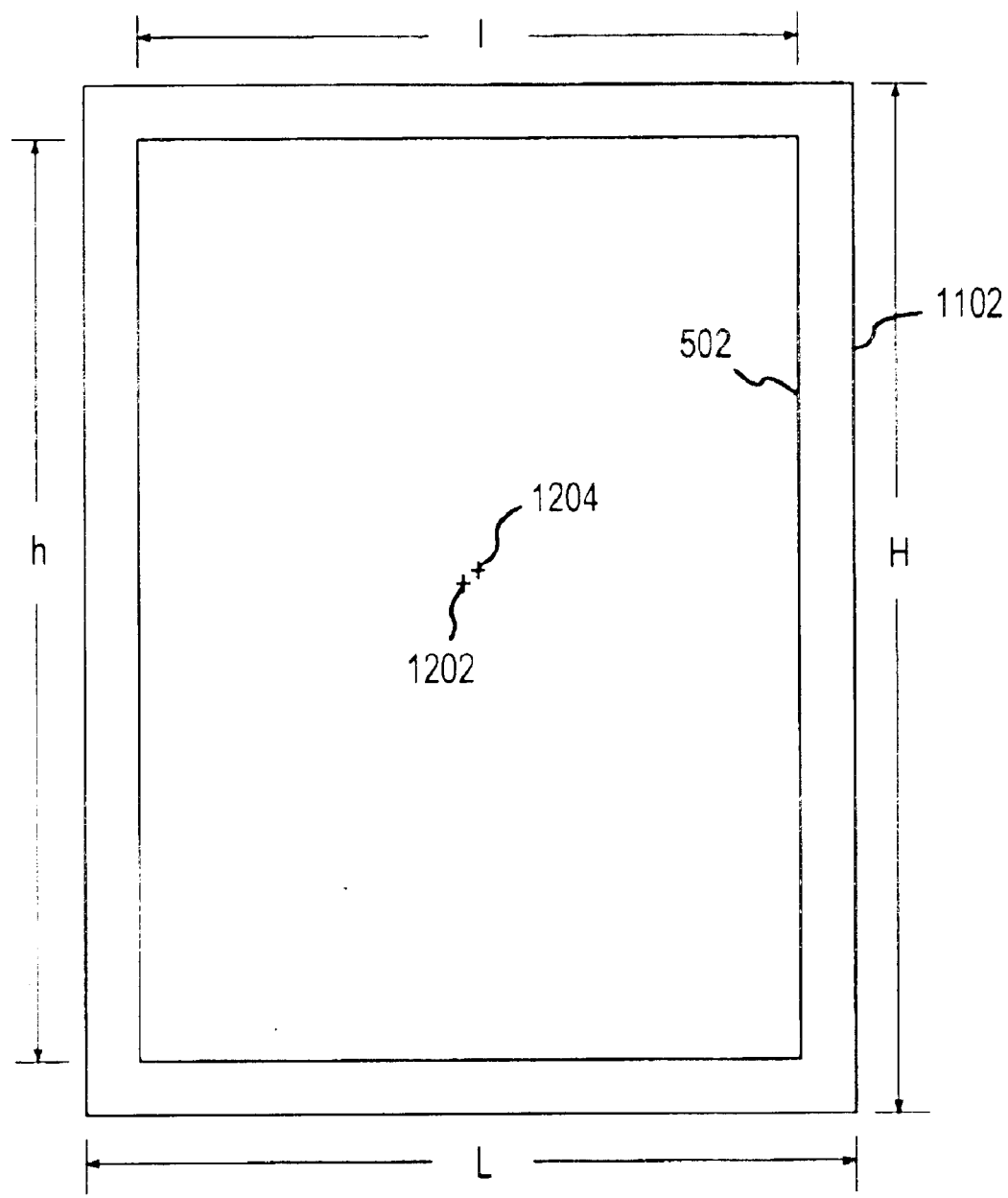
FIG. 12 depicts exemplary vapor-dispensing device geometries.

Referring to FIG. 12, faceplate perimeter 502 is characterized by a center (or centroid) 1202 and height and length dimensions h and l respectively. Similarly, housing perimeter 1102 is characterized by a center (or centroid) 1204 and height and length dimensions H and L respectively. Faceplate perimeter 502 has an aspect ratio defined as H/L, and housing perimeter 1102 has an aspect ratio defined as h/l. In accordance with one aspect of the present invention, center 1202 substantially coincides with center 1204. In accordance with a further aspect of the present invention, the aspect ratio of faceplate perimeter 502 is substantially equal to the aspect ratio of housing perimeter 1102. In one embodiment, for example, the faceplate aspect ratio is substantially equal to the aspect ratio of a standard dual-outlet faceplate, e.g., between approximately 1.3 and 1.7, preferably about 1.5. It will appreciated that the aspect ratio may be define in any convenient matter depending upon the shape of the respective faceplate and housing.

Although the invention has been described herein in conjunction with the appended drawings, those skilled in the art will appreciate that the scope of the invention is not so limited. Modifications in the selection, design, and arrangement of the various components and steps discussed herein may be made without departing from the scope of the invention.

What is claimed is:

1. A refill component for use with a vapor-dispensing device configured to connect to an electrical receptacle, wherein the vapor-dispensing device has a housing having a front surface and a back surface separated by a thickness t, wherein the back surface has a minor axis dimension x and a major axis dimension y, wherein a first device outlet and a second device outlet is provided on the front surface of the housing, and wherein the first and second device outlets are separated by an inter-outlet distance d, and wherein a plug extends from the back surface of the housing for connecting to the electrical receptacle, said refill component comprising:

a refill body having a thickness less than t, wherein x/d is between approximately 2.0 and 2.5; y/d is between approximately 3.0 and 3.5; t/d is between approximately 0.5 and 1.0, said refill body removeably connected to said vapor-dispensing device.

2. The apparatus of claim 1, wherein said refill component at least partially surrounds said first and second outlets.

3. The apparatus of claim 2, wherein said refill is generally "U"-shaped.

4. The apparatus of claim 2, wherein the refill is configured to slideably attach to the environment-altering apparatus.

5. The apparatus of claim 2, wherein said refill is a rectangular ring.

6. The apparatus of claim 1, wherein said environment-altering apparatus is passive.

7. The apparatus of claim 1, wherein said environment-altering apparatus is active.

* * * * *